United States Patent [19]

Wheeler et al.

[11] 4,304,714

[45] Dec. 8, 1981

[54] POLYFUNCTIONAL PHENOLIC OXAMIDE ANTIOXIDANTS

[75] Inventors: Edward L. Wheeler, Watertown; Elmar H. Jancis, Naugatuck; Richard A. Gencarelli, Middletown; Franklin H. Barrows, Beacon Falls, all of Conn.

[73] Assignee: Uniroyal, Inc., New York, N.Y.

[21] Appl. No.: 43,761

[22] Filed: May 30, 1979

Related U.S. Application Data

[63] Continuation-in-part of Ser. No. 931,087, Aug. 4, 1978, abandoned.

[51] Int. Cl.³ .................... C08K 5/20; C07C 103/84
[52] U.S. Cl. ............................ 260/45.85 B; 560/75
[58] Field of Search ................ 260/45.85 B; 560/75

[56] References Cited

U.S. PATENT DOCUMENTS 4,145,556  3/1979  Hirsch et al. ............... 260/45.85 B
4,154,723  5/1979  Hirsch ......................... 260/45.85 B

*Primary Examiner*—V. P. Hoke
*Attorney, Agent, or Firm*—Paul H. Ginsburg; Thomas A. Beck; Andrew D. Maslow

[57] ABSTRACT

Novel phenolic oxamide antioxidants for protecting organic materials such as synthetic and natural rubbers, petroleum products, and plastics from oxidative degradation.

6 Claims, No Drawings

POLYFUNCTIONAL PHENOLIC OXAMIDE ANTIOXIDANTS

BACKGROUND OF THE INVENTION

This application is a continuation-in-part of abandon U.S. application Ser. No. 931,087 filed Aug. 4, 1978.

The present invention relates to novel phenolic oxamides which are useful in protecting organic materials such as synthetic and natural rubbers, petroleum products, and plastics from oxidative degradation.

SUMMARY OF THE INVENTION

The present invention relates to compounds of the formula $R^1COOANHCOR^2$ wherein A is $C_2$ to $C_5$ alkylene substituted with one or two $OCO(CH_2)_mR^3$ groups, wherein $R^3$ is 3-W-5-Y-4-hydroxyphenyl wherein W and Y may be the same or different and are $C_1$ to $C_{12}$ alkyl and m is 0, 1 or 2, $R^1$ is $-(CH_2)_mR^3$, $C_1$ to $C_{20}$ alkyl, $C_4$–$C_8$ cycloalkyl, preferably $C_5$ to $C_6$ cycloalkyl, $C_6$ to $C_{10}$ aryl, or phenyl substituted with halogen, $C_1$ to $C_{12}$ alkyl, $C_1$ to $C_{12}$ alkoxy, nitro, or hydroxy, and $R^2$ is $-CONHAOCOR^1$ wherein A and $R^1$ are as defined above. The terms alkoxy, alkylene and alkyl comprise linear and branched moieties; the term cycloalkyl includes bridged groups and non-bridged groups.

The above described invention may be represented by the following formula:

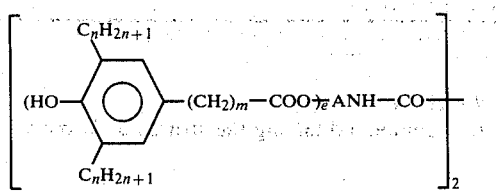

wherein A is a branched $C_3$–$C_7$ alkylene, m is 0, 1 or 2, n is an integer from 1 to 12, e has a value of 2 or 3.

The present invention also relates to a process for preparing a compound having the formula $R^1COOANHCOR^2$, wherein A is $C_2$ to $C_5$ alkylene substituted with one or two $CH_2OCO(CH_2)_mR^3$, wherein $R^3$ is 3-W-5-Y-4-hydroxyphenyl wherein W and Y may be the same or different and are $C_1$ to $C_{12}$ alkyl and m is 0, 1 or 2; $R^1$ is $C_1$ to $C_{20}$ alkyl, $C_4$ to $C_8$ cycloalkyl, preferably $C_5$ to $C_6$ cycloalkyl, $C_6$ to $C_{10}$ aryl, phenyl substituted with halogen, $C_1$ to $C_{12}$ alkyl, $C_1$ to $C_{12}$ alkoxy, nitro or hydroxy, or $R^1$ is $-(CH_2)_mR^3$ wherein $R^3$ and m are defined above; and $R^2$ is $-CONHAOCOR^1$, wherein A and $R^1$ are as defined above; comprising reacting a compound of the formula $H_2NQ(OH)_s$, wherein s is an is 2 or 3 and 3 and Q is trivalent or tetravalent $C_2$–$C_{12}$ alkylene with (1) a compound having the formula $(COX)_2$, wherein X is halogen, hydroxy or $C_1$ to $C_3$ alkoxy, at a temperature of from 5° to 250° C. and a pressure of from 100 Pa to 10 kPa for 2 to 24 hours, and then the resulting intermediate with (2) a compound having the formula $R^1COX$, wherein $R^1$ and X are as defined above, at a temperature from 15° to 250° C. and a pressure from 100 Pa to 10 kPa for 2 to 24 hours, provided that if X is halogen, steps (1) and (2) are carried out in the presence of an acid acceptor.

The present invention also relates to a compound of the formula $R_1COOANH_2$ wherein A is $C_2$ to $C_5$ alkylene substituted with one or two $-CH_2OCO(CH_2)_mR^3$ groups, wherein $R^3$ is 3-W-5-Y-4-hydroxyphenyl, wherein W and Y may be the same or different and are $C_1$ to $C_{12}$ alkyl and m is 0, 1 or 2; and $R_1$ is a group $-(CH_2)_mR^3$ wherein m and $R^3$ are as defined above.

The present invention also relates to a compound of the formula $[CONHQ(OH)_s]_2$, wherein s is an integer from 2 to 3 and Q is trivalent or tetravalent $C_2$–$C_{12}$ alkylene.

The present invention also relates to compositions comprising the compounds of the present invention and organic materials subject to oxidative degradation.

The compounds of the present invention are useful in stabilizing organic materials normally subject to oxidative degradation. Materials that are thus stabilized include a multitude of synthetic polymers. Among those polymers are various polyolefins such as polyethylene, polypropylene, polybutylene, polybutadiene, polymethylpentene. Other polymers stabilized by the compounds of the present invention include acetal resins, polyacrylates, polymethacrylates, polydialkylpthalate, cellulosics, polyamides, polyesters, polyurethanes, polycarbonate, polystyrene, polyvinyl chloride, polyvinylidene chloride. Copolymers can also be stabilized by the compounds of the present invention. Representative copolymers include ethylene/propylene copolymers, butadiene/styrene copolymers, ethylene/vinyl acetate copolymers, and ethylene/ethyl acrylate copolymers. Copolymers also include terpolymers such as ethylene/propylene/non-conjugated diene terpolymer and acrylonitrile/butadiene/styrene interpolymers. Polymer blends such as polystyrene/polyphenylene oxide and ethylenepropylene copolymer or terpolymer/polypropylene can also be stabilized by the compounds of the present invention. Other materials stabilized by compounds of the present invention include hot melt adhesives such as those based on polyesters, polyamides or ethylene/vinyl acetate. Also stabilized are petroleum products such as fuels, lubricating oils, petrolatum jellies, and natural products such as natural rubber, waxes, fat, tallow, linseed oil, corn oil, cottonseed oil, and codliver oil. The preceding list is representative, though by no means exhaustive, of the products that can benefit from the compounds of the present inventions. To achieve protection against oxidative degradation, the compounds of the present invention are added in the amounts generally used for known antioxidants which may have similar properties to achieve such protection. Depending on the substrate used, the antioxidant is added in amounts of 0.001 to 10 percent by weight based on the weight of the substrate, with the usual range being from 0.05 to 2.0 percent.

The compounds of the present invention can be used by themselves to stabilize organic materials, or they can be used in combination with other stabilizers. Such other stabilizers might include other phenolics, thio compounds of various kinds, such as thiodipropionate esters, phosphites and phosphonates, anti-copper chemicals such as oxalamides, ultraviolet stabilizers of various kinds as well as other additives where the use of such additives has been found beneficial.

The compounds of the present invention can generally be made from known starting materials by amidification and esterification reactions well known in the literature. Convenient aminoalcohols used in the preparation of the compounds of the present invention include: 2-amino-2-methyl-1,3-propanediol, 2-amino-2- ethyl-1,3-propanediol, tris(hydroxymethyl)aminomethane, 3-amino-1,2-propanediol, 2-aminomethyl-2-methyl-1,3-propanediol, 2,2,2-tris-(hydroxyethyl)aminoethane. Many other aminoalcohols are readily made by known methods from available starting materials.

A convenient synthesis of a compound of the present invention would generally include making the amide from one of the aforementioned alkanolamines followed by esterification of the hydroxyalkylamide. The amide can readily be prepared by reacting the alkanolamine with oxalic acid, acid chloride or ester.

The usual starting material for esterification is a 3,5-dialky-4-hydroxybenzoic acid, a 2-(3,5-dialkyl-4-hydroxyphenyl)acetic acid or a 3-(3,5-dialkyl-4-hydroxyphenyl)propionic acid, or an acid chloride or ester of the aforementioned starting materials.

The preparations indicated above are mentioned as non-limiting examples of ways to carry out the objects of this invention. Other methods will suggest themselves to those skilled in the art.

The following non-limiting examples further illustrate the preparation and use of the compounds of the present invention.

EXAMPLE 1

N,N$^1$-bis[tris(hydroxymethyl)methyl]oxamide

A mixture of 60.5 g (0.5 mole) tris(hydroxymethyl)aminomethane and 36.6 g (0.25 mole) ethyl oxalate was refluxed in one liter ethanol for six hours. The white precipitate was removed by filtration and was dried in a forced air oven at 60° C. The title compound weighed 52 g (87% yield) and melted at 216°–218° C. with decomposition.

EXAMPLE 2

N,N$^1$-oxalyldiamido-bis-{isobutanetriyl tris[3(3,5-ditert.-butyl-4-hydroxyphenyl)propionate]}

N,N$^1$-bis[tris(hydroxymethyl)methyl]oxamide prepared according to Example 1 is esterified by a reaction with 3-(3,5-di-t-butyl-4-hydroxyphenyl)propionic acid chloride.

EXAMPLE 3

N,N$^1$-bis[1,1-bis(hydroxymethyl)ethyl]oxamide

To a solution of 52.5 g (0.5 mole) 2-amino-2-methyl-propanediol-1,3 in 400 ml ethanol was added 36.5 g (0.25 mole) diethyloxalate. An exothermic reaction ensued. The title compound precipitated on cooling. It was filtered and air dried. The yield of product melting at 219°–220° C. was 59 g (89.4%).

EXAMPLE 4

N,N$^1$-oxalyldiamido-bis{2-methyltrimethylene-bis[3(3,5-di-tert.-butyl-4-hydroxyphenyl)propionate]}

A mixture of 26.4 g (0.1 mole) N,N$^1$-bis-[1,1-bis(hydroxymethyl)ethyl]oxamide, 116.8 g (0.4 mole) ethyl 3(3,5-di-tert.-butyl-4-hydroxyphenyl)propionate and butanestannoic acid was heated under vacuum 4 hours at 160° C. and 13 hours at 170° C. The reaction mixture was recrystallized twice from a mixture of toluene and hexane. The title compound melted at 157°–160° C.

EXAMPLE 5

This example shows the usefulness of the compounds of the present invention in polypropylene. It also shows the beneficial effect observed by using the compounds of the present invention in conjunction with a co-stabilizer. The particular compound used in each run of this Example and of the succeeding Examples is identified by the number of one of the above Examples in which the preparation of the compound is described.

The stabilizers were incorporated into Profax 6501 (trademark) polypropylene resin on a mill at 166° C. Seventy-five mil plaques (discs approximately one inch in diameter and 75 mil (1.0 mm) thick) were prepared by compression molding in a press at 27,000 psi (186 MPa) and 177° C. These specimens were placed in a forced air oven at 149° C., and the number of days required for embrittlement to occur was noted. When two out of three buttons embrittled (that is, they became granular due to heat aging), the specimen was considered to have failed. The results are shown in Table I.

TABLE 1

| Compound/Co-Stabilizer | Concentration* | Days to Failure |
|---|---|---|
| none | — | 1 |
| DSTDP** | 0.2 | 4 |
| Example 2 | 0.1 | 35 |
| Example 4 | 0.1 | 39 |
| Example 2/DSTDP | 0.1/0.1 | 46 |
| Example 4/DSTDP | 0.1/0.1 | 83 |

*Parts by weight per hundred parts by weight of polypropylene
**Distearyl thiodipropionate

We claim:
1. A compound having the structural formula:

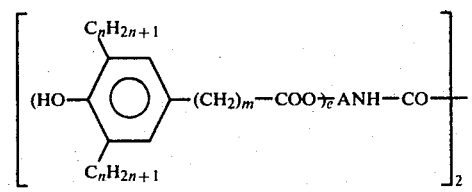

wherein A is a branched $C_3$–$C_7$ alkylene, m is 0, 1 or 2, n is an integer from 1 to 12, e has a value of 2 or 3.

2. A compound according to claim 7 wherein m is 2 and n is 4.

3. N,N$^1$-oxalyldiamidobis(2-methyltrimethylenebis[3-(3,5-di-tert-butyl-4-hydroxyphenyl)propionate].

4. N,N$^1$-oxalyldiamidobis(isobutanetriyltris [3-(3,5-di-tert-butyl-4-hydroxyphenyl)propionate]).

5. A composition comprising an organic material subject to oxidative degradation and an oxidative degradation inhibiting amount of a compound according to claim 1, 2, 3 or 4.

6. A method of inhibiting the oxidative degradation of an organic material comprising adding to said material an oxidative degradation inhibiting amount of a compound according to claim 1, 2, 3 or 4.

* * * * *

UNITED STATES PATENT AND TRADEMARK OFFICE
CERTIFICATE OF CORRECTION

PATENT NO. : 4,304,714
DATED : December 8, 1981
INVENTOR(S) : Edward L. Wheeler, et al It is certified that error appears in the above-identified patent and that said Letters Patent are hereby corrected as shown below:

In claim 2 delete "7" and insert in its place -- 1 --.

Signed and Sealed this

Nineteenth Day of October 1982

[SEAL]

Attest:

Attesting Officer

GERALD J. MOSSINGHOFF

Commissioner of Patents and Trademarks